United States Patent
Elder et al.

(10) Patent No.: US 8,071,078 B2
(45) Date of Patent: *Dec. 6, 2011

(54) ENCAPSULATED COLORANTS FOR NATURAL SKIN APPEARANCE

(75) Inventors: S. Todd Elder, Butler, NJ (US); Christina Ligia Andrianov, Monroe, NY (US)

(73) Assignee: BASF SE, Ludwigshafen (DE)

( * ) Notice: Subject to any disclaimer, the term of this patent is extended or adjusted under 35 U.S.C. 154(b) by 1356 days.

This patent is subject to a terminal disclaimer.

(21) Appl. No.: 10/943,184

(22) Filed: Sep. 16, 2004

(65) Prior Publication Data

US 2005/0031558 A1    Feb. 10, 2005

Related U.S. Application Data

(63) Continuation-in-part of application No. 10/785,208, filed on Feb. 24, 2004, now abandoned.

(60) Provisional application No. 60/450,197, filed on Feb. 26, 2003.

(51) Int. Cl.
   *A61K 8/00*      (2006.01)
   *A61K 8/18*      (2006.01)

(52) U.S. Cl. .......................... 424/59; 424/63

(58) Field of Classification Search .................... None
See application file for complete search history.

(56) References Cited

U.S. PATENT DOCUMENTS

| | | | |
|---|---|---|---|
| 4,879,175 A | 11/1989 | Ugro, Jr. | 428/321.5 |
| 5,234,711 A | 8/1993 | Kamen et al. | 427/213.34 |
| 5,320,835 A * | 6/1994 | Pahlck et al. | 424/64 |
| 5,382,433 A | 1/1995 | Pahlck et al. | 424/401 |

FOREIGN PATENT DOCUMENTS

| | | |
|---|---|---|
| EP | 0225799 | 6/1987 |
| EP | 0445342 | 9/1991 |
| WO | 91/06277 | 5/1991 |
| WO | 98/50002 | 11/1998 |
| WO | 01/37803 | 5/2001 |
| WO | WO0154809 * | 8/2001 |
| WO | 01/80823 | 11/2001 |
| WO | 02/090445 | 11/2002 |
| WO | 03/080005 | 10/2003 |

* cited by examiner

*Primary Examiner* — Tracy Vivlemore
*Assistant Examiner* — Jennifer Berrios
(74) *Attorney, Agent, or Firm* — Shiela Loggins; Joseph Suhadolnik

(57) ABSTRACT

The present invention relates to personal care or cosmetic compositions that contain a blend of at least 2 microencapsulated colorants that produces a natural, textured tone effect. A method for cosmetic treatment comprises application of such personal care or cosmetic compositions onto at least a part of the body.

16 Claims, No Drawings

ENCAPSULATED COLORANTS FOR NATURAL SKIN APPEARANCE

This application is a continuation-in-part of application Ser. No. 10/785,208, filed Feb. 24, 2004, abandoned, which claims the benefit of U.S. Provisional Application No. 60/450,197, filed Feb. 26, 2003.

FIELD OF THE INVENTION

This invention relates to compositions containing encapsulated coloring agent blends and their use in personal care applications.

BACKGROUND OF THE INVENTION

It is known to encapsulate hydrophobic liquids by dispersing the hydrophobic liquid into an aqueous medium containing a melamine formaldehyde pre-condensate and then reducing the pH, resulting in an impervious aminoplast resin shell wall surrounding the hydrophobic liquid. Such microcapsules are preferably used to provide encapsulated inks for use in pressure sensitive carbonless copy paper. However, since these microcapsules are based on melamine formaldehyde resins, there is a risk that under certain conditions formaldehyde may be evolved, which is undesirable.

U.S. Pat. No. 5,234,711 describes a method for encapsulation of pigment particles utilized in ink formulations and their use for cosmetic products. The cosmetic products are especially directed to eye liner pens.

U.S. Pat. No. 5,382,433 and published PCT Application WO 98/5002 describe the use of a cosmetic stick that contains microencapsulated pigment particles. The encapsulated pigment in the '433 patent is made by coacervation polymerization. The PCT application expands on this patent by including a volatile solvent in the cosmetic composition. The volatile solvent is represented to minimize the gritty feel of the microencapsulated material.

A variety of techniques are known for providing encapsulated or entrapped colorants. For example, published PCT Application WO 91/06277 describes cosmetic formulations which have activatable dormant pigments dispersed in an anhydrous base or vehicle. Ground pigment or liquid carrier dispersion is microencapsulated to form stable, dry, free flowing powder of micro-sized particles. The preferred process of encapsulation is by coacervation e.g. by emulsifying a liquid dispersion in a continuous, external aqueous phase to form micro-sized droplets and a complex of colloidal material is added to the external phase in such a way to form a deposit on or around each droplet thereby forming an outer wall or shell. The microcapsules are intended to rupture and release the dormant pigment when subjected to physical forces.

U.S. Pat. No. 5,234,711 concerns methods of encapsulating pigment particles useful in manufacturing of cosmetic products. It is an objective of this disclosure to employ an encapsulation process for increasing the wettability, dispersibility and heat resistance of the pigment particles. The method encapsulation involves redox or free radical vinyl polymerization in an aqueous medium.

Published European Patent Application 225,799 describes microencapsulated solid non-magnetic colorant material in a liquid, gel, waxy or low temperature melting solid carrier phase, which is encapsulated within a polymeric shell. Absorbed onto the shell is a silane or titanate coupling agent, which increases the oleophilicity of the surface of the solid colorant material.

Published European Patent Application 445,342 relates to a cosmetic composition comprising a pigment that has been formed by incorporating a solvate dye into a resin and admixing with a cosmetic carrier. The amount of pigment present is sufficient to provide attractive amount of pigment present sufficient to provide an attractive cosmetic effect when applied to skin, nails or hair. Any cosmetically acceptable soluble dye can be used. Any resin may be used provided it can be pulverized to a fine powder. The solvate dye may be incorporated into the resin by adding to the elasticized or molten resin, or by dissolving the dye in a solution of unpolymerized resin and mutual solvent for the dye and the resin, then polymerizing the resin, or by contacting the dye with the resin. The dye impregnated resin powders are said to be used in a variety of cosmetic compositions WO 02/090445 addresses the problem of color retention and provides polymeric particles comprising a matrix polymer and colorant distributed throughout it. The matrix polymer is formed from a blend of monomers comprising a first monomer, which is an ethylenically unsaturated ionic monomer, which is a salt of a volatile counterion, and a second monomer, which is an ethylenically unsaturated hydrophobic monomer, which is capable of forming a homopolymer of glass transition temperature in excess of 50° C. Typical matrix polymers include copolymers that have been formed from styrene with ammonium acrylate. The polymeric particles exhibit good retention properties and are able to retain the colorant under a variety of conditions. The obtained particles are stated to be useful in a variety of industrial processes, for instance in the manufacture of inks, paper and cosmetics.

The prior art does not describe the use of a blend of microencapsulated coloring agents in cosmetic compositions that produce a textured natural tone coloring when applied, or creates similar effects on or in the cosmetic product itself.

SUMMARY OF THE INVENTION

The present invention provides an improved personal care or cosmetic composition that comprises a liquid personal care or cosmetic formulation having an effective amount of a blend of encapsulated coloring agents wherein the microencapsulated colorants have a particle size between 1 and 50 microns, and wherein the blend of microencapsulated colorants are selected from at least two colors that are distinct from each other.

The present invention also provides a method of use that comprises application of a liquid personal care or cosmetic formulation having an effective amount of an encapsulated coloring agent as described above to at least a part of said body.

DETAILED DESCRIPTION OF THE INVENTION

The microencapsulated particles according to the first aspect of the invention and the products resulting from the process according to the second aspect of the invention have enhanced visual performance, and furthermore the polymer matrix does not allow any of the entrapped colorant to be released even under prolonged use.

The polymeric products can be further enhanced if the polymeric matrix is cross-linked. This cross-linking can be as a result of including a cross-linking step in the microencapsulation process. This can be achieved by including self cross-linking groups in the polymer, for instance monomer repeating units carrying a methylol functionality.

Preferably though the cross-linking is achieved by including a cross-linking agent with the aqueous phase polymer.

The cross-linking agents are generally compounds which react with functional groups on the polymer chain. For instance when the polymer chain contains anionic groups, suitable cross-linking agent may include aziridines, diepoxides, carbodiamides, silanes and multivalent metals, for instance aluminum or zirconium. One particularly preferred cross-linking agent is ammonium zirconium carbonate. Another particularly preferred class of cross-linking agents includes compounds which form covalent bonds between polymer chains, for instance silanes or diepoxides.

The cross-linking process desirably occurs during the dehydration step. Thus where a cross-linking agent is included, it will generally remain dormant until the dehydration is started.

Polymers formed from the special combination of a hydrophobic monomer that is capable of forming a homopolymer having a glass transition temperature in excess of 50° C., preferably greater than 60 or 80° C., exhibit considerably improved performance in regard to the impermeability to the colorant. By hydrophobic monomer is meant that the monomer has solubility in water of less than 5 g per 100 ml water.

Glass transition temperature ($T_g$) for a polymer is defined in the Encyclopedia of Chemical Technology, Volume 19, Fourth Edition, page 891 as the temperature below which (1) the transitional motion of entire molecules and (2) the coiling and uncoiling of 40 to 50 carbon atom segments of chains are both frozen. Thus below its $T_g$ a polymer would not exhibit flow or rubber elasticity. The $T_g$ of a polymer may be determined using Differential Scanning Calorimetry (DSC). Thus a reference sample with a known $T_g$ and the experimental sample are heated separately but in parallel according to a linear temperature program. The two heaters maintain the two samples at identical temperatures. The power supplied to the two heaters to achieve this is monitored and the difference between them plotted as a function of reference temperature, which translates as a recording of the specific heat as a function of temperature. As the reference temperature is increased or decreased and the experimental sample approaches a transition the amount of heat required to maintain the temperature will be greater or lesser depending on whether the transition is endothermic or exothermic.

Generally the average particle size diameter of the particles is less than about 100 microns. Usually the average particle size diameter tends to be smaller, for instance less than 70 or 80 microns, often less than 40 or 50 microns and typically the average particle diameter will be between 750 nanometers and 40 microns.

Preferably the average particle size diameter is in the range 10 to 40 microns, usually between 20 and 40 microns. Average particle size is determined by a Coulter particle size analyzer according to standard procedures well documented in the literature.

Without being limited to theory it is believed that the particular combination of ionic monomer and said hydrophobic monomer provides polymers with the right degree of hydrophilicity and hardness that seems to be responsible for the improvements in impermeability to the colorant.

Specific examples of said hydrophobic monomers include styrene, methyl methacrylate, tertiary butyl methacrylate, phenyl methacrylate, cyclohexyl methacrylate and isobornyl methacrylate.

It has been found that it is not possible to replace the hydrophobic monomers with ethylenically unsaturated carboxylic acid esters that are not capable of forming a homopolymer that has a glass transition temperature of at least 50° C. without adversely increasing the permeability of the polymer. Preferably still the $T_g$ should be at least 60° C. or even at least 80° C. For instance substituting the hydrophobic monomer of the present invention by other (meth) acrylic esters, for instance 2-ethylhexyl acrylate would be unsuitable. Best results are generally obtained by use of monomers that are capable of forming polymers of very high $T_g$.

Therefore less preferred products would be produced using ethyl acrylate or propyl acrylate as the hydrophobic monomer.

The ionic monomer may contain either anionic or cationic groups or alternatively may be potentially ionic, for instance in the form of an acid anhydride. Preferably the ionic monomer is an ethylenically unsaturated anionic or potentially anionic monomer. Suitable anionic monomer include (meth) acrylic acid, maleic acid, maleic anhydride, itaconic acid, itaconic acid anhydride, crotonic acid, (meth) allyl sulfonic acid, vinyl sulfonic acid and 2-acrylamido-2-methyl propane sulfonic acid. Preferred anionic monomers are carboxylic acids or acid anhydrides.

When the ionic monomer is anionic, for instance a carboxylic acid or anhydride, the volatile counterion may be ammonia or a volatile amine component. Thus the polymer may be produced in free acid form and then neutralized with an aqueous solution of ammonium hydroxide or a volatile amine, for instance ethanolamine.

Alternatively the polymer may be prepared by copolymerizing the ammonium or volatile amine salt of an anionic monomer with the hydrophobic monomer.

Generally any suitable polymerization process may prepare the matrix polymer. For instance the polymer can be conveniently prepared by aqueous emulsion polymerization for instance as described in EP-A-697423 or U.S. Pat. No. 5,070,136. The polymer can then be neutralized by the addition of an aqueous solution of ammonium hydroxide or a volatile amine.

In a typical polymerization process the blend of hydrophobic monomer and anionic monomer is emulsified into an aqueous phase which contains a suitable amount of emulsifying agent. Typically the emulsifying agent may be any commercially available emulsifying agent suitable for forming aqueous emulsion.

Desirably these emulsifying agents will tend to be more soluble in the aqueous phase than in the monomer water-immiscible phase and thus will tend to exhibit a high hydrophilic lipophilic balance (HLB). Emulsification of the monomer may be effected by known emulsification techniques, including subjecting the aqueous/nonaqueous phase to vigorous stirring or shearing or alternatively passing the aqueous/nonaqueous phase through a screen or mesh. Polymerization may then be effected by use of suitable initiator systems, for instance a UV initiator or thermal initiator. Suitable techniques of initiating the polymerization would be to elevate the temperature of the aqueous emulsion of monomer to above 70 or 80° C. and then add between 50 and 1000 ppm ammonium persulfate by weight of monomer.

Generally the matrix polymer has a molecular weight of up to 200,000 (determined by GPC using the industry standard parameters). Preferably the polymer has a molecular weight of below 50,000, for instance 2,000 to 20,000.

Usually the optimum molecular weight for the matrix polymer is around 8,000 to 12,000. Typically the monomer blend may contain at least 50% by weight hydrophobic monomer, the remainder being made up of anionic monomer. Generally though the hydrophobic monomer will be present in amounts of at least 60% by weight.

Preferred compositions contain between 65 and 90% by weight hydrophobic polymer, for instance around 70 or 75%.

A particularly preferred matrix polymer is a transparent or translucent copolymer of styrene with ammonium acrylate. More preferably this polymer is used when the process employs a cross-linking agent, which is especially ammonium zirconium carbonate.

In an alternative version of the process of the present invention the ionic monomer may be cationic or potentially cationic, for instance an ethylenically unsaturated amine. In this form of the invention the volatile counterionic component is a volatile acid component. Thus in this form of the invention the matrix polymer can be formed in an analogous way to the aforementioned anionic matrix polymer, except that the anionic monomer is replaced by a cationic or potentially cationic monomer. Generally where the polymer is prepared in the form of a copolymer of a free amine and hydrophobic monomer, including a suitable volatile acid, for instance acetic acid, formic acid or even carbonic acid, neutralizes it. Preferably the polymer is neutralized by a volatile carboxylic acid. The amount of cationic or potentially cationic monomer to hydrophobic monomer is generally the same as for the aforementioned anionic monomer.

The particles may entrap one or more colorants and the colorant may be any colorant, for instance a dye, pigment or lake. Typically suitable colorants include any organic or inorganic pigment or colorant approved for use in cosmetics by CTFA and the FDA such as lakes, iron oxides, titanium dioxide, iron sulfides or other conventional pigments used in cosmetic formulations. Examples of the pigment include inorganic pigments such as carbon black, D&C Red 7, calcium lake, D&C Red 30, talc lake, D&C Red 6, barium lake, russet iron oxide, yellow iron oxide, brown iron oxide, talc, kaolin, mica, mica titanium, red iron oxide, magnesium silicate and titanium oxide; and organic pigments such as Red No. 202, Red No. 204, Red No. 205, Red No. 206, Red No. 219, Red No. 228, Red No. 404, Yellow No. 205, Yellow No. 401, Orange No. 401 and Blue No. 404. Examples of vat dyes are Red No. 226, Blue No. 204 and Blue No. 201. Examples of lake dyes include various acid dyes, which are laked with aluminum, calcium or barium.

Preferably the colorant is an aqueous solution of a water soluble dye. Suitable dyes for the present invention include FD&C Blue No. 11, FD&C Blue No. 12, FD&C Green No. 13, FD&C Red No. 13, FD&C Red No. 140, FD&C Yellow No. 15, FD&C Yellow No. 16, D&C Blue No. 14, D&C Blue No. 19; D&C Green No. 15, D&C Green No. 16, D&C Green No. 18, D&C Orange No. 14, D&C Orange No. 15, D&C Orange No. 110, D&C Orange No. 111, D&C Orange No. 117, FD&C Red No. 14, D&C Red No. 16, D&C Red No. 17, D&C Red No. 18, D&C Red No. 19, D&C Red No. 117, D&C Red No. 119, D&C Red No. 121, D&C Red No. 122, D&C Red No. 127, D&C Red No. 128, D&C Red No. 130, D&C Red No. 131, D&C Red No. 134, D&C Red No. 139, FD&C Red No. 140, D&C Violet No. 12, D&C Yellow No. 17, Ext. D&C Yellow No. 17, D&C Yellow No. 18, D&C Yellow No. 111, D&C Brown No. 11, Ext. D&C Violet No. 12, D&C Blue No. 16 and D&C Yellow No. 110. Such dyes are well known, commercially available materials, with their chemical structure being described, e.g., in 21 C. F. R. Part 74 (as revised Apr. 1, 1988) and the CTFA Cosmetic Ingredient Handbook, (1988), published by the Cosmetics, Toiletry and Fragrances Association, Inc. These publications are incorporated herein by reference.

The colorant can be a substance which is a dormant colorant, for instance a color former that exhibits a color on exposure to a suitable trigger mechanism, for instance heat or irradiation. Suitably such entrapped color formers can be coated onto or incorporated into suitable substrates and then treated to exhibit the color. The advantage of providing color formers as polymeric particles is that they can be more easily be processed and incorporated into the substrate in a desired way. The color former can still be activated even though it is entrapped within the polymer particle.

Any inorganic or organic pigment or colorant approved for use in cosmetics is particularly preferred for use in the present invention. Preferred pigments include the lakes, iron oxides, titanium dioxide and hydrophobic dyes. Certified dyes can be water soluble or lakes. Lakes are organic pigments prepared by precipitating a soluble dye on a reactive or absorbent stratum, which is an essential part of the pigment's composition. Most lakes are aluminum, barium or calcium derived. These insoluble pigments are used mostly in makeup products, either powders or liquids, when a temporary color is desired that won't stain the skin (as oil-soluble dyes tend to do). The lakes are used in these products along with inorganic colors such as iron oxide, zinc oxide and titanium dioxide (the whitest white pigment).

Water soluble, certified dyes are used mostly in color products, although it is possible to make a temporary hair color rinse using only certified dyes. When incorporating these dyes in an emulsion, they will be soluble in the external water phase in an oil/water system. It is useful to know the solubility properties of the certified dyes in various solvents and their stability to reactive chemicals.

Color Additives subject to certification and permanently listed for food, drug and/or cosmetic use.

The following tables list currently available dyes and colorants approved for use in food, drugs and/or cosmetics. The selected coloring agent for use herein is preferably selected from the following exemplary lists.

TABLE I

Dyes certified for use in foods, drugs, cosmetics (FDC colors)

| | | |
|---|---|---|
| FD&C Blue No. 1 | FD&C Green No. 3 | FD&C Red No. 4 |
| FD&C Red No. 40 | FD&C Yellow No. 5 | FD&C Yellow No. 6 |

TABLE 2

Dyes certified for topically applied drugs and cosmetics

| | | |
|---|---|---|
| Ext. DC Violet #2 | Ext. D&C Yellow No. 7 | Ext. D&C Violet No. 2 |
| D&C Brown No. 1 | FD&C Red No. 4 | D&C Red No. 17 |
| D&C Red No. 31 | D&C Red No. 34 | D&C Red No. 39 |
| D&C Violet No. 2 | D&C Blue No. 4 | D&C Green No. 6 |
| D&C Green No. 8 | D&C Yellow No. 7 | D&C Yellow No. 8 |
| D&C Yellow No. 11 | D&C Orange No. 4 | D&C Orange No. 10 |
| D&C Orange No. 11 | | |

TABLE 3

Dyes certified for drugs and foods only

| | | |
|---|---|---|
| D&C Blue No. 4 | D&C Brown No. 1 | D&C Green No. 5 |
| D&C Green No. 6 | D&C Green No. 8 | D&C Orange No. 4 |
| D&C Orange No. 5 | D&C Orange No. 10 | D&C Orange No. 11 |
| D&C Red No. 6 | D&C Red No. 7 | D&C Red No. 17 |
| D&C Red No. 21 | D&C Red No. 22 | D&C Red No. 27 |
| D&C Red No. 28 | D&C Red No. 30 | D&C Red No. 31 |
| D&C Red No. 33 | D&C Red No. 34 | D&C Red No. 36 |
| D&C Violet No. 2 | D&C Yellow No. 7 | D&C Yellow No. 8 |
| D&C Yellow No. 10 | D&C Yellow No. 11 | |

Some color additives are exempt from certification and permanently listed for cosmetic use, including aluminum powder, annatto, bismuth oxychloride, bronze powder, caramel, carmine, beta-carotene, chromium hydroxide green, chromium oxide green copper (metallic powder), dihydroxyacetone, disodium EDTA-copper, ferric ammonium ferrocyanide, ferric ferrocyanide, guanine (pearl essence), guaiazulene (azulene), iron oxides, luminescent zinc sulfide, manganese violet, mica, pyrophyllite, silver (for coloring fingernail polish), titanium dioxide, ultramarines (blue, green, pink, red & violet), and zinc oxide.

The process of the present invention involves dispersing the aqueous solution of matrix polymer containing colorant into a water immiscible liquid. Typically the water immiscible liquid is an organic liquid or blend of organic liquids. The preferred organic liquid is a mixture of non-volatile paraffin oil and volatile paraffin oil. The two oils may be used in equal proportions by weight, but generally it is often preferred to use the non-volatile oil in excess, for instance greater than 50 to 75 parts by weight of the non-volatile oil to 25 to less than 50 parts by weight of the volatile oil.

In the process according to the second aspect of the invention it is desirable to the present invention to include a polymeric amphipathic stabilizer in the water-immiscible liquid. The amphipathic stabilizer may be any suitable commercially available amphipathic stabilizer, for instance HYPERMER (RTM) (available from ICI). Suitable stabilizers also include the stabilizers described in WO-A-97/24179.

Although it is possible to include other stabilizing materials in addition to the amphipathic stabilizer, such as surfactants, it is generally preferred that the sole stabilizing material is the amphipathic stabilizer.

In the process of the present invention the dehydration step can be achieved by any convenient means. Desirably subjecting the dispersion in oil to vacuum distillation can effect dehydration. Generally this will require elevated temperatures, for instance temperatures of 30° C. or higher. Although it may be possible to use much higher temperatures e.g. 80 to 90° C. it is generally preferred to use temperatures of below 60 or 70° C.

Instead of vacuum distillation it may be desirable to effect dehydration by spray drying. Suitably this can be achieved by the spray drying process described in WO-A-97/34945. The dehydration step removes water from the aqueous solution of matrix polymer and also the volatile counterion component, resulting in a dry polymer matrix which is insoluble and non-swellable in water, containing therein the colorant, which is distributed throughout the polymeric matrix.

It has now been found that applying a personal care or cosmetic formulation composition comprising a blend of microencapsulated coloring agents incorporated therein produces desirable effects upon application. Notably, the compositions containing a blend of microencapsulated color agents having unique and distinct colors, particularly a blend of more than one primary color are effective means for producing natural, textured skin tone effects. The primary colors are understood to mean red, yellow and blue. Blends comprising red and yellow primary colors are preferred. An additional feature of these encapsulates would be the elimination of milling or grinding often encountered with nonencapsulated colorants.

The personal care composition according to the invention comprises from 0.1 to 40% by weight, for example from 1 to 20% by weight, and especially from 2 to 15% by weight based on the total weight of the composition, of the microencapsulated coloring agents as well as a cosmetically tolerable carrier or adjuvant. While water is cosmetically tolerable, and in most instances will also be present, the phrase "a cosmetically tolerable carrier or adjuvant" is intended to refer to at least one substance other than water that is customarily employed in personal care or cosmetic compositions.

Encapsulated microsphere average diameters of 0.1 to 50 microns are preferred, for example 5 to 40 and especially 10 to 30 microns.

The personal care or cosmetic preparation according to the invention may be formulated as a water-in-oil or oil-in-water emulsion, as an alcoholic or alcohol-containing formulation, as a vesicular dispersion of an ionic or non-ionic amphiphilic lipid, as a gel, or a solid stick; preferably the cosmetic preparation is in the form of a liquid.

As a water-in-oil or oil-in-water emulsion, the cosmetically tolerable adjuvant contains preferably from 5 to 50% of an oily phase, from 5 to 20% of an emulsifier and from 30 to 90% water. The oily phase may contain any oil suitable for cosmetic formulations, e.g. one or more hydrocarbon oils, a wax, natural oil, silicone oil, a fatty acid ester or a fatty alcohol.

Cosmetic liquids may contain mono- or polyols such as ethanol, isopropanol, propylene glycol, hexylene glycol, glycerol or sorbitol.

Cosmetic formulations according to the invention may be contained in a wide variety of cosmetic preparations. Especially the following preparations, for example, come into consideration:

shaving preparations, e.g. shaving soap, foaming shaving creams, non-foaming shaving creams, foams and gels, preshave preparations for dry shaving, aftershaves or aftershave lotions;

skin-care preparations, e.g. skin emulsions, multi-emulsions or skin oils and body powders;

cosmetic personal care preparations, e.g. facial make-up in the form of lipsticks, eye shadow, liquid make-up, day creams or powders, facial lotions, creams and powders (loose or pressed);

light-protective preparations, such as sun tan lotions, creams and oils, sun blocks and pretanning preparations;

deodorants, e.g. deodorant sprays, pump-action sprays, deodorant gels, sticks or roll-ons;

antiperspirants, such as antiperspirant sticks, creams or roll-ons; and solid/liquid personal cleaning products, such as soap, cleansers, shampoo and conditioners.

Depending upon the form of the personal care preparation, it will comprise, in addition to the encapsulated coloring agents, further constituents, for example sequestering agents, additional non-encapsulated colorings, perfumes, thickening or solidifying (consistency regulator) agents, emollients, UV absorbers, skin-protective agents, antioxidants and preservatives.

Compositions according to the invention may be prepared by physically blending suitable encapsulated coloring agents into personal care formulations by methods which are well known in the art. The examples illustrate several of such methods.

In one embodiment of the method, the personal care or cosmetic formulation comprises from 0.1 to 40% by weight, for example from 1 to 20% by weight, and especially from 2 to 15% by weight based on the total weight of the formulation, of the microencapsulated coloring agent.

In one embodiment of the method, the personal care or cosmetic composition comprises a blend of microencapsulated coloring agents that are individually provided in a single polymeric matrix material. In another, the personal care or cosmetic composition comprises a blend of microcapsules as described above containing different microencapsulated coloring agents that are individually provided in separate polymeric matrix materials.

In one embodiment of the method, the personal care or cosmetic composition is formulated as a water-in-oil or oil-in-water emulsion, as an alcoholic or alcohol-containing formulation, as a vesicular dispersion of an ionic or non-ionic amphiphilic lipid, as a gel, or a solid stick.

In various embodiments of the method, the personal care or cosmetic composition is in the form of a shaving preparation, a skin-care preparation, a cosmetic personal care preparation, a light-protective preparation, a deodorant or antiperspirant, or personal cleaning product.

The following examples describe certain embodiments of this invention, but the invention is not limited thereto. It should be understood that numerous changes to the disclosed embodiments could be made in accordance with the disclosure herein without departing from the spirit or scope of the invention. These examples are therefore not meant to limit the scope of the invention. Rather, the scope of the invention is to be determined only by the appended claims and their equivalents. In these examples all parts given are by weight unless otherwise indicated.

EXAMPLE 1

An aqueous solution is formed by dissolving 10 grams of FD&C Blue No. 1 in 396 g of 25% solution of a copolymer of styrene and ammonium acrylate (65/35 weight % monomers ratio, molecular weight about 6,000) and then addition of 9.9 g of 50% ammonium zirconium carbonate. An oil solution is prepared by mixing 50 g of 20% Lopol® polymeric emulsion stabilizer (available from Ciba Specialty Chemicals), 89 g of Kristol M14 oil and 70.4 g of Isopar G solvent. The aqueous solution is added to the agitated oil solution and then homogenized with a high shear SILVERSON mixer to form a water-in-oil emulsion. After 15 minutes of emulsification, an extra 179 g of Isopar G is added as a diluent.

The resulting emulsion is transferred to a resin pot having vacuum distillation capabilities. The emulsion is warmed to 25° C. and the water/ISOPAR G mixture distilled under reduced pressure a constant temperature of about 30° C. The volume of water and solvent is monitored and distillation continued until no further water is collected in the distillate. Then the temperature is allowed to rise to 100° C. without vacuum. The dried dye polymer particles in oil are then held at 100° C. for 60 minutes to drive off ammonia and to crosslink the carboxylated styrene based matrix polymer to the water-insoluble form. The contents of the flask are then cooled. The dispersion of dye polymer particles in oil is stable and has an average of diameter of less than 2 microns. They may be collected and dried if desired.

EXAMPLE 2

Example 1 is repeated with the exception that 10 grams of a water-soluble red (FD&C Red No. 7) is used in place of the FD&C Blue No. 1 dye. A red dye polymer particle dispersion in oil is obtained.

EXAMPLE 3

Example 1 is repeated with the exception that 10 grams of a red pigment (FD&C Red No. 7, aluminum lake) is dispersed in the aqueous solution of the polymer solution. A dispersion in oil of the red pigment microencapsulated in a polymer matrix was obtained.

EXAMPLE 4

Example 1 is repeated with the exception that 10 grams of a yellow pigment (D&C Yellow No. 10, aluminum lake) is dispersed in the aqueous solution of the polymer solution. A dispersion in oil of the yellow pigment microencapsulated in the polymer matrix is obtained.

EXAMPLE 5

Example 1 is repeated with the exception that 8 grams of a yellow pigment (D&C Yellow No. 10, aluminum lake) and 2 grams of a red pigment (FD&C Red No. 7, aluminum lake) are dispersed in the aqueous solution of the polymer solution. A dispersion in oil of the mixed yellow and red pigments microencapsulated in the polymer matrix is obtained.

EXAMPLE 6

| | | Lipstick | | |
|---|---|---|---|---|
| Phase | INCI Name | Trade Name | Supplier | Parts |
| A | Castor Oil | Lipovol CO | Lipo | 33.25 |
| A | Triethylhexanoin | Schercemol GTO | Scher | 7.50 |
| A | Triisostearyl Trilinoleate | Schercemol TIST | Scher | 15.00 |
| A | Triisostearyl Citrate | Schercemol TISC | Scher | 17.50 |
| A | Euphorbia Cerifera (Candelilla) Wax | Refined Candelilla Wax Prills | Ross Waxes | 7.00 |
| A | Copernicia Cerifera (Carnauba) Wax | Yellow Carnuba Wax Flakes | Ross Waxes | 1.80 |
| A | Ozokerite | White Ozokerite Wax 77W | Ross Waxes | 1.80 |
| A | Microcyrstalline Wax | Microcrystalline Wax 1275W | Ross Waxes | 3.50 |
| A | Hydroxylated Lanolin | Ritahydrox | Rita | 1.00 |
| A | Methylparaben | Nipagin M | Clariant | 0.20 |
| A | Propylparaben | Nipasol M | Clariant | 0.10 |
| B | Colorant | Encapsulated Red Pigment | Ciba Specialty Chemicals | 5.70 |
| B | Colorant | Encapsulated Yellow Pigment | Ciba Specialty Chemicals | 1.10 |
| B | Colorant | Encapsulated Blue Pigment | Ciba Specialty Chemicals | 0.20 |

Lipstick -continued

| Phase | INCI Name | Trade Name | Supplier | Parts |
|---|---|---|---|---|
| B | Mica | Cosmetic BC Mica # 280 | Whittacker, Clark & Daniels | 4.35 |
| | | | Total | 100.0 |

Procedure:

Phase A is combined, heated between 90-105° C., and mixed until uniform. Phase B is then added with stirring until homogenous. The temperature is maintained above 70° C. as the lipstick is poured into the mold.

EXAMPLE 7

| | Medium Protection Sunscreen | | | |
|---|---|---|---|---|
| Phase | INCI Name | Trade name | Supplier | Parts |
| A | Deionized Water | DI Water | N/A | 84.86 |
| A | Propylene Glycol (and) Diazolidinyl Urea (and) Methylparaben (and) Propylparaben | Germaben II | ISP | 1.00 |
| A | Aloe Barbadensis Leaf Juice | Aloe Gel 1:1 Natural | Tri-K Industries | 1.00 |
| A | Propylene Glycol | Propylene Glycol | Dow Chemical | 2.50 |
| A | Butylene Glycol (and) Water (and) Juglans Nigra (Black Walnut) Shell Extract | Actiphyte of Black Walnut Hull | Active Organics | 0.04 |
| A | Ethyhexyl Salicylate | Escalol 587 | ISP | 5.00 |
| A | Ethylhexyl Methoxycinnamate | Escalol 557 | ISP | 3.00 |
| B | Sodium Acrylates Copolymer (and) Paraffinum Liquidum (and) PPG-1 Trideceth-6 | Ciba ® SALCARE ® SC91 | Ciba Specialty Chemicals | 2.00 |
| C | Colorant | Encapsulated Red Pigment | Ciba Specialty Chemicals | 0.20 |
| C | Colorant | Encapsulated Blue Pigment | Ciba Specialty Chemicals | 0.10 |
| D | Fragrance | Flowers in the mist | Belle Aire Fragrances | 0.30 |
| | | | Total | 100.00 |

Procedures:

In an appropriate vessel add Part A and start moderate agitation.

Add part B and mix until uniform.

Add Part C, than part D and mix until well blended.

EXAMPLE 8

| | Talc Free Loose Face Powder | | | |
|---|---|---|---|---|
| Phase | INCI Name | Trade Name | Supplier | Parts |
| A | Mica | Sericite PHN | Presperse | 81.45 |
| A | Polymethyl Methacrylate | Ganzpearl GM-0600W | Presperse | 5.00 |
| A | Synthetic Wax and Corn Gluten Protein | Microease 110XF | Presperse | 2.00 |
| A | Titanium Dioxide | Titanium Dioxide 3228 | Whittaker, Clark & Daniels | 5.00 |
| A | Methylparaben | Nipagin M | Clariant | 0.20 |
| A | Propylparaben | Nipasol M | Clariant | 0.10 |
| A | Imidazolidinyl Urea | Germall 115 | ISP | 0.25 |

-continued

| Talc Free Loose Face Powder | | | | |
|---|---|---|---|---|
| Phase | INCI Name | Trade Name | Supplier | Parts |
| B | Colorant | Encapsulated Red Pigment | Ciba Specialty Chemicals | 1.00 |
| B | Colorant | Encapsulated Yellow Pigment | Ciba Specialty Chemicals | 5.00 |
| | | | Total | 100.00 |

Procedure:

Mill together A until fully dispersed. Add B to A and blend until uniform.

EXAMPLE 9

| Oil in Water Facial Foundation | | | | |
|---|---|---|---|---|
| Phase | INCI Name | Trade Name | Supplier | Parts |
| A | Deionized water | DI Water | N/A | 53.94 |
| A | 10% KOH solution | 10% KOH solution | N/A | 1.30 |
| A | PEG-12 Dimethicone | DC 193 Surfactant | Dow Corning | 0.10 |
| A | Talc | Talc | Whittaker, Clark & Daniels | 0.72 |
| B | 1,3-Butylene Glycol | Jeechem BUGL | Jeen Int. | 4.00 |
| B | Magnesium Aluminum Silicate | Veegum Granules | R. T. Vanderbilt | 1.00 |
| C | 1,3-Butylene Glycol | Jeechem BUGL | Jeen Int. | 2.00 |
| C | Cellulose Gum | CMC 7MF | Hercules | 0.12 |
| C | Methylparaben | Nipagin M | Clariant | 0.02 |
| D | Di-PPG-3 Myristyl Ether Adipate | Cromollient DP3-A | Croda | 14.00 |
| D | Diethyl Hexyl Maleate | Pelemol DOM | Phoenix | 4.00 |
| D | Steareth-10 | Lipocol S-10 | Lipo | 2.00 |
| D | Steareth-2 | Lipocol S-2 | Lipo | 0.50 |
| D | Cetyl Alcohol | Crodacol C-95 NF | Croda | 0.62 |
| D | Dicetyl Phosphate and Ceteth-10 Phosphate and Ceteryl Alcohol | Crodafos CES | Croda | 4.00 |
| D | Propyl Paraben | Nipasol M | Clariant | 0.10 |
| E | Colorant | Encapsulated TiO2 | Ciba Specialty Chemicals | 7.50 |
| E | Colorant | Encapsulated Yellow Pigment | Ciba Specialty Chemicals | 2.50 |
| E | Colorant | Encapsulated Red Pigment | Ciba Specialty Chemicals | 1.20 |
| E | Colorant | Encapsulated Blue Pigment | Ciba Specialty Chemicals | 0.20 |
| F | DMDM Hydantoin | Mackstat DM | McIntyre Group | 0.18 |
| | | | Total | 100.0 |

Procedure:

Combine ingredients in phase A using a homogenizer and begin heating to 80° C. Add phase B and C and homogenize for 1 hour. In a separate beaker combine ingredients in phase D, heat to 80° C. and mix until uniform. After all ingredients in phase D have become uniform slowly add to the main phase while continuing to homogenize. Upon complete addition of phase D, homogenize for 15 min at 80° C. then begin cooling the mixture. At 60° C. switch to paddle mixing using moderate agitation. Phase E is added and mixed until homogenous mixture obtained. At 50° C. phase F is added. The mixture is cooled until it reaches room temperature.

EXAMPLE 10

| Press Powder Eye Shadow (purple) | | | |
|---|---|---|---|
| INCI Name | Trade Name | Supplier | Parts |
| Mica | Sericite PHN | Presperse | 75.60 |
| Zinc Stearate | Zinc Stearate | Witco | 5.00 |
| Colorant | Encapsulated TiO2 | Ciba Specialty Chemicals | 6.00 |

Press Powder Eye Shadow (purple) (continued)

| INCI Name | Trade Name | Supplier | Parts |
|---|---|---|---|
| Colorant | Encapsulated Red Pigment | Ciba Specialty Chemicals | 2.00 |
| Colorant | Encapsulated Blue Pigment | Ciba Specialty Chemicals | 0.60 |
| Methylparaben | Nipagin M | Clariant | 0.20 |
| Propylparaben | Nipasol M | Clariant | 0.10 |
| Calcium Aluminum Borosilicate | Luxsil | Presperse | 5.00 |
| PEG-4 Diheptanoate | Liponate 2-DH | Lipo | 5.50 |
| | | Total | 100.00 |

Procedure:

Combine ingredients and mix well. Heat to 100° C. and press at 2000 psi.

EXAMPLE 11

Nail Enamel (purple)

| Phase | INCI Name | Trade name | Supplier | Parts |
|---|---|---|---|---|
| A | Butyl Acetate and Toluene and Nitrocellulose and Tosylamide/Formadlehyde Resin and Isopropyl Alcohol and Dibutyl Phthalate and Ethyl acetate and Camphor and n-Butyl Alcohol and Silica and Quaterinium-18 Hectorite | Suspending Lacquer SLF-2 | Engelhard | 86.00 |
| A | Butyl Acetate (and) Bismuth Oxychloride (and) Nitrocellulose (and) Isopropyl Alcohol (and) Stearylalkonium Hectorite | Biju Ultra UXD | Engelhard | 2.25 |
| A | Mica (and) Titanium Dioxide | Flamenco Ultra Sparkle 4500 | Engelhard | 1.00 |
| A | Colorant | Encapsulated Red Pigment | Ciba Specialty Chemicals | 1.25 |
| A | Colorant | Encapsulated Blue Pigment | Ciba Specialty Chemicals | 1.25 |
| A | Dimethicone | Dow Corning 200 | Dow Corning | 1.00 |
| A | Tosylamide/Epoxy Resin | Lustrabrite S-70 | Telechemische | 4.00 |
| B | Butyl Acetate | Butyl Acetate | Dow Chemical | 1.17 |
| B | Ethyl Acetate | Ethyl Acetate | Dow Chemical | 0.42 |
| B | Toluene | Toluene | Shell | 1.66 |
| | | | Total | 100.00 |

Procedure:

Combine phase A and mix until uniform. Combine phase B in a separate vessel and mix until uniform. Add phase B to phase A with stirring until uniform.

What is claimed is:

1. A personal care or cosmetic composition comprising a blend of microencapsulated colorants wherein the microencapsulated colorants comprise a colorant or dormant colorant which dormant colorant exhibits color upon exposure to heat or radiation encapsulated by a polymeric matrix material formed from a blend of monomers comprising a first monomer that is an ethylenically unsaturated ionic monomer and a second monomer that is an ethylenically unsaturated hydrophobic monomer selected from styrene, methyl methacrylate, tertiary butyl methacrylate, phenyl methacrylate, cyclohexyl methacrylate and isobornyl methacrylate, said material selected to prevent the release of the colorant or dormant colorant, have a particle size between 1 and 50 microns, and wherein the blend of microencapsulated colorants are selected from at least two colors that are distinct from each other, wherein the personal or cosmetic composition is in the form of a shaving preparation, a skin-care preparation, a cosmetic personal care preparation, a light-protective preparation, a deodorant or antiperspirant, or a personal cleaning product.

2. A composition according to claim 1 wherein the blend of microencapsulated colorants is selected from at least two primary colors.

3. A composition according to claim 2 wherein the primary colors are red and yellow.

4. A composition according to claim 1, wherein the blend of microencapsulated colorants comprises from 0.1 to 40% by weight based on the total weight of the composition.

5. A composition according to claim 1, wherein the microencapsulated colorants comprise a polymeric matrix material that encapsulates a natural dye, synthetic dye, organic pigment, or inorganic pigment.

6. A composition according to claim 1, which comprises from 0.1 to 35% by weight based on the total weight of the composition, of the blend of microencapsulated colorants.

7. A composition according to claim 6, which is formulated as a water-in-oil or oil-in-water emulsion, as an alcoholic or alcohol-containing formulation, as a vesicular dispersion of an ionic or non-ionic amphiphilic lipid, as a gel, or a solid stick.

8. A composition according to claim 6, which comprises at least one further constituent selected from the group consisting of sequestering agents, non-encapsulated colorings, perfumes, thickening or solidifying (consistency regulator) agents, emollients, UV absorbers, skin-protective agents, antioxidants and preservatives.

9. A method for cosmetic treatment of a body, comprising application of a personal care or cosmetic composition comprising a blend of microencapsulated colorants wherein the microencapsulated colorants comprise a colorant or dormant colorant which dormant colorant exhibits color upon exposure to heat or radiation encapsulated by a polymeric matrix material formed from a blend of monomers comprising a first monomer that is an ethylenically unsaturated ionic monomer and a second monomer that is an ethylenically unsaturated hydrophobic monomer selected from styrene, methyl methacrylate, tertiary butyl methacrylate, phenyl methacrylate, cyclohexyl methacrylate and isobornyl methacrylate, said material selected to prevent the release of the colorant or dormant colorant, have a particle size between 1 and 50 microns, and wherein the blend of microencapsulated colorants are selected from at least two colors that are distinct from each other onto at least a part of said body.

10. A method according to claim 9, wherein the blend of microencapsulated colorants comprises from 0.1 to 40% by weight based on the total weight of the composition.

11. A method according to claim 9, wherein the microencapsulated colorant comprises a polymeric matrix material that encapsulates a natural dye, synthetic dye, organic pigment, or inorganic pigment.

12. A method according to claim 9, wherein the personal care or cosmetic composition is in the form of a shaving preparation, a skin-care preparation, a cosmetic personal care preparation, a light-protective preparation, a deodorant or antiperspirant or a personal cleaning product.

13. A method according to claim 12, which comprises from 0.1 to 40% by weight based on the total weight of the composition, of the blend of microencapsulated colorants.

14. A method according to claim 13, which is formulated as a water-in-oil or oil-in-water emulsion, as an alcoholic or alcohol-containing formulation, as a vesicular dispersion of an ionic or non-ionic amphiphilic lipid, as a gel, or a solid stick.

15. A method according to claim 14, which further comprises at least one further constituent selected from the group consisting of sequestering agents, non-encapsulated colorings, perfumes, thickening or solidifying (consistency regulator) agents, emollients, UV absorbers, skin-protective agents, antioxidants and preservatives.

16. A method according to claim 9, wherein the personal care or cosmetic composition comprises a blend of microencapsulated coloring agents that are individually provided in a single polymeric matrix material.

* * * * *